United States Patent [19]
Müller et al.

[11] Patent Number: 6,087,536
[45] Date of Patent: Jul. 11, 2000

[54] PREPARATION OF INDENE DERIVATIVES

[75] Inventors: Hans-Joachim Müller, Grünstadt; Peter Trübenbach, Ludwigshafen; Bernhard Rieger, Ulm; Jürgen Matthäus Wagner, Dornstadt; Ulf Dietrich, Ulm, all of Germany

[73] Assignee: BASF Aktiengesellschaft, Ludwigshafen, Germany

[21] Appl. No.: 08/916,349

[22] Filed: Aug. 22, 1997

[30] Foreign Application Priority Data

Aug. 28, 1996 [DE] Germany ............... 19 634 684

[51] Int. Cl.$^7$ ................................. C07D 45/00
[52] U.S. Cl. .......................................... 568/319
[58] Field of Search ............................. 568/319

[56] References Cited

U.S. PATENT DOCUMENTS

| | | | |
|---|---|---|---|
| 5,329,049 | 7/1994 | Weisse et al. | 568/319 |
| 5,360,936 | 11/1994 | Weisse et al. | 568/319 |
| 5,455,366 | 10/1995 | Rohrmann et al. | 556/8 |

FOREIGN PATENT DOCUMENTS 2084016  5/1993  Canada .

OTHER PUBLICATIONS

March, Jerry—"Advanced Organic Chemistry—Reactions, Mechanisms, and Structure", 4th Edition, pp. 534–540 & 1162–1164, 1992.

Primary Examiner—Mukund J. Shah
Assistant Examiner—Tamthom N. Truong
Attorney, Agent, or Firm—Keil & Weinkauf

[57] ABSTRACT

A process for preparing indene derivatives of the general formula I

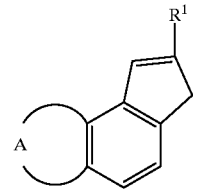

I where
$R^1$ is a $C_1$–$C_{10}$-alkyl radical, a phenyl radical or a $C_1$–$C_4$-alkyl-substituted phenyl radical and
A is a bridge which, together with the adjacent carbons, forms a six-membered aromatic or a five- or six-membered heteroaromatic or carbocyclic ring onto which a further aromatic ring may be fused,
comprises reacting II with III

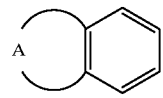

II

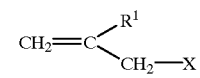

III (X=chlorine, bromine, iodine) in the presence of a Friedel-Crafts catalyst to give IV

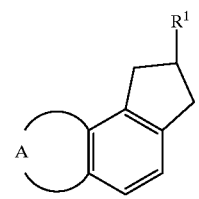

IV which is then dehydrogenated to I.

7 Claims, No Drawings

PREPARATION OF INDENE DERIVATIVES

The present invention relates to a process for preparing indene derivatives of the general formula I

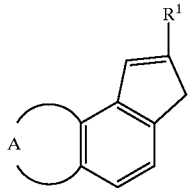

I where $R^1$ is a $C_1$–$C_{10}$-alkyl radical, a phenyl radical or a $C_1$–$C_4$-alkyl-substituted phenyl radical and A is a bridge which, together with the adjacent carbons, forms a six-membered aromatic or a five- or six-membered heteroaromatic or carbocyclic ring onto which a further aromatic ring may be fused.

Indene derivatives of the general formula I are important precursors for metallocene complexes used as polymerization catalysts. For this purpose, the indene derivatives are reacted with transition metals, in particular with zirconium salts, and with metallocenium ion formers to give the corresponding metallocene complexes.

Substituted indenes can be prepared by various processes. Conventionally, an intermediate indanone derivative is prepared and converted into the corresponding indene derivative by reduction and dehydration.

EP-A1-549 900 describes the synthesis of a substituted benzindanone. In a multi-step synthesis, the five-membered ring is formed by reaction with a malonic ester, alkaline hydrolysis of the diester, thermal decarboxylation, chlorination of the remaining carboxyl group and intramolecular Friedel-Crafts acylation. Owing to its multi-step character, the synthesis is technically very complicated.

EP-A1-567 953 describes a synthesis of indanone derivatives wherein the five-membered ring is formed by reacting an appropriate benzene derivative with a substituted acrylic ester in liquid hydrogen fluoride. EP-A1-587 107 describes the preparation of 2-methylbenzindanone by reacting naphthalene with methacrylic anhydride in the presence of $BF_3$/ hydrogen fluoride. Owing to the problematic handling of the highly toxic hydrofluoric acid, these synthetic routes again involve considerable technical complications.

A further synthetic route for indanones is described in EP-A1-545 304. In this instance, the preparation is carried out by reacting a benzene derivative with α-haloalkylpropionyl halides, preferably with α-bromoisobutyryl bromide.

Disadvantages of these syntheses are the complicated, multi-step process, the large amount of halogen-containing wastes and the use of some very toxic reactants.

It is an object of the present invention to provide a simple synthetic route for preparing indene derivatives of the general formula I without the disadvantages of the known synthetic routes.

We have found that this object is achieved by a process for preparing indene derivatives of the general formula I

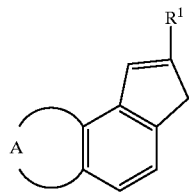

I where $R^1$ is a $C_1$–$C_{10}$-alkyl radical, a phenyl radical or a $C_1$–$C_4$-alkyl-substituted phenyl radical and A is a bridge which, together with the adjacent carbons, forms a six-membered aromatic or a five- or six-membered heteroaromatic or carbocyclic ring onto which a further aromatic ring may be fused, which comprises reacting a compound II

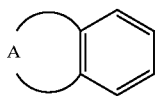

II with a compound III

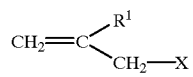

III where X is chlorine, bromine or iodine in the presence of a Friedel-Crafts catalyst to give a compound IV

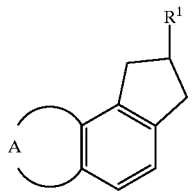

IV which is then dehydrogenated to the indene derivative I.

The substituent $R^1$ is introduced into the indene derivatives via the compound III. $R^1$ is preferably methyl or ethyl, particularly preferably methyl; however, other $C_1$–$C_{10}$-alkyl radicals, the phenyl radical or $C_1$–$C_4$-alkyl-substituted phenyl radicals are also suitable. In addition to the abovementioned $C_1$–$C_4$-alkyl radicals, suitable $C_1$–$C_{10}$-alkyl radicals also include the various isomers of pentyl, hexyl, heptyl, octyl, nonyl and decyl radicals. In addition to the preferred unsubstituted phenyl radical, suitable phenyl radicals are in particular monomethyl- or monoethyl-substituted phenyl radicals.

The radical X in the compound III may be chlorine, bromine or iodine; preferably, X is bromine.

Together with the two adjacent carbons, the bridge A forms a six-membered aromatic or a five- or six-membered heteroaromatic or carbocyclic ring. By choosing the appropriate bridge A, substituted rings and unsubstituted rings can be formed. Bridges A leading to unsubstituted rings are for example the structural elements

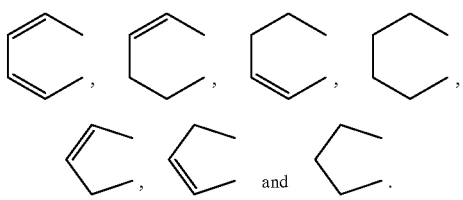

Suitable substituents for these structural elements are for example $C_1$–$C_4$-alkyl, $C_1$–$C_4$-fluoroalkyl, silyl, $C_1$–$C_4$-alkylsilyl, phenyl and benzyl, the $C_1$–$C_4$-alkyl groups including methyl, ethyl, n-propyl, isopropyl, n-butyl, isobutyl, sec-butyl and tert-butyl.

Preference is given to bridges A of the structure

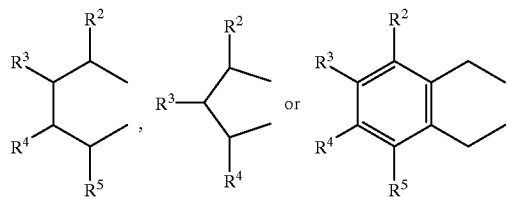

where the radicals $R^2$ to $R^5$ are each hydrogen, $C_1$–$C_4$-alkyl, $C_1$–$C_4$-fluoroalkyl, silyl, $C_1$–$C_4$-alkylsilyl, phenyl or benzyl, again including the above-described alkyl radicals.

Preference is further given to a process which comprises using a compound IIa

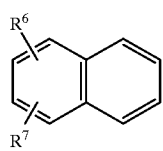

IIa where $R^6$ and $R^7$ each have the meanings of $R^2$ to $R^5$ as compound II.

Preferred radicals $R^6$ and $R^7$ are hydrogen and, from the alkyl radicals, the isopropyl radical. However, preference is given to unsubstituted compounds IIa.

The catalyst used in the first step of the process according to the invention is a Friedel-Crafts catalyst. Suitable Friedel-Crafts catalysts are all customary catalysts of this kind, for example $AlCl_3$, $AlBr_3$, $ZnCl_2$, $FeCl_3$, $SnCl_4$, $SbCl_5$, $TiCl_4$, $SiCl_4$, $BF_3$ and $PCl_5$; preference is given to using $AlCl_3$.

The catalyst is preferably employed in such an amount that the molar ratio of catalyst to the compound III is from 0.1:1 to 1.5:1, preferably from 0.2:1 to 1.0:1.

Suitable solvents for the process according to the invention are all customary solvents. These are in particular chlorinated hydrocarbons such as methylene chloride; 1,2-dichloroethane, 1,1,2,2-tetrachloroethane and chlorobenzene; particular preference is given to using methylene chloride as solvent.

In the process according to the invention, the reaction of the compounds II and III to give the compounds IV is preferably commenced at low temperatures, especially preferably at from −80 to 0° C., in particular at from −40 to −10° C. Subsequently, i.e. at the earliest after all reactants have been added, the reaction may also be continued at slightly higher temperatures, for example at from 0° C. to 50° C., preferably at 20–30° C.

In this process step, pressure is not a critical parameter, so that this step is generally carried out at atmospheric pressure.

Suitable processes for dehydrogenating the indane derivative IV to the indene derivative I include all conventional processes for dehydrogenating hydrocarbon chains to compounds carrying a double bond in conjugation to aromatic rings. Suitable catalysts are in particular platinum and palladium catalysts, and preference is given to carrying out this reaction in the presence of finely divided elemental platinum, for example platinum black.

In the dehydrogenation of the compound IV to the indene derivative I, preference is given to using cyclopentene or cyclohexene, particularly preferably cyclopentene, as hydrogen acceptor. However, other cyclic or open-chain olefins can also be used for this purpose.

This second reaction step is preferably carried out at elevated temperatures, for example at from 50 to 150° C., particularly preferably at from 80 to 120° C.

It is advantageous to carry out the reaction under superatmospheric pressure, i.e. in an autoclave. The pressure is generally predetermined by the temperature and the solvents include. Suitable solvents include all inert solvents, for example hexane, cyclohexane, heptane, octane, particularly preferably cyclohexane.

EXAMPLES

Example 1

Preparation of 2-methylbenzindane

A solution of 20 g (166 mmol) of naphthalene in 50 ml of methylene chloride was added dropwise to a mixture of 22.13 g of $AlCl_3$ (166 mmol) and 22.41 g of 3-bromoisobutene (166 mmol) in 250 ml of the same solvent. During the addition, the temperature was kept at −10° C. After the addition had ended, the mixture was stirred at room temperature for 12 h and then hydrolyzed with 100 ml of water and acidified with 50 ml of conc. HCl. After the separation, the aqueous phase was extracted with methylene chloride and the combined organic phases were extracted with water. The methylene chloride was removed from the solution under reduced pressure and the residue was dissolved in toluene. The solids were separated off and the solution obtained was neutralized using $K_2CO_3$ and dried with $Na_2SO_4$. To remove byproducts, the filtrate obtained was chromatographed over silica gel 60.

Yield: 11 g (36%), $^1$H-NMR spectrum (200 MHz, $CDCl_3$): 1.25 (d, 3H); 1.93 (m, 1H); 2.4 (m, 2H); 2.6 (m, 2H); 6.6–7.25 (m, 6H).

Example 2

Preparation of 2-methylbenzindene

A solution of 2-methylbenzindane (19 g, 104 mmol) in 100 ml of cyclohexane and 50 ml of cyclopentene was heated in an autoclave in the presence of freshly prepared platinum black at 100° C. for 8 hours. After the solution had cooled and the solvent had been removed, the crude product was chromatographed over silica gel 60. After the solvent had been distilled off, the product was obtained as an oil.

Yield: 9.77 g (52%).

We claim:

1. A process for preparing indene derivatives of the general formula I

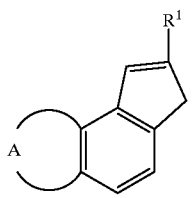

where

R$^1$ is a C$_1$–C$_{10}$-alkyl radical, a phenyl radical or a C$_1$–C$_4$-alkyl-substituted phenyl radical and A is a bridge which, together with the adjacent carbons, forms a six-membered aromatic or a five- or six-membered heteroaromatic or carbocyclic ring onto which a further aromatic ring may be fused, which comprises reacting a compound II

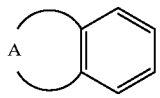

with a compound III

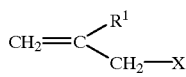

where X is chlorine, bromine or iodine, in the presence of a Friedel-Crafts catalyst to give a compound IV

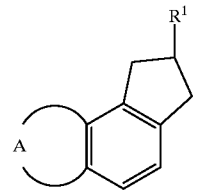

which is then dehydrogenated to the indene derivative I.

2. A process as claimed in claim 1, wherein the bridge A has the structure

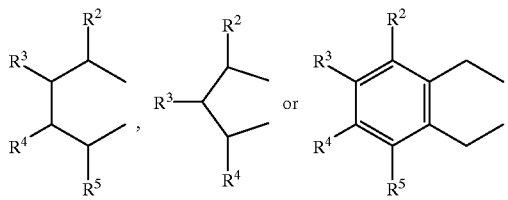

where the radicals R$^2$ to R$^5$ are each hydrogen, C$_1$–C$_4$-alkyl, C$_1$–C$_4$-fluoroalkyl, silyl, C$_1$–C$_4$-alkylsilyl, phenyl or benzyl.

3. A process as claimed in claim 2, wherein the compound II used is a compound IIa

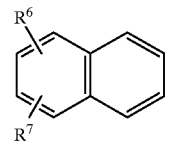

where R$^6$ and R$^7$ each have the meanings of R$^2$ to R$^5$.

4. A process as claimed in claim 1, wherein R$^1$ is methyl or ethyl.

5. The process as claimed in claim 1, wherein the Friedel-Crafts catalyst used is AlCl$_3$.

6. A process as claimed in claim 1, wherein the reaction of the compounds II and III to give the compound IV is commenced at from −80 to 0° C.

7. A process as claimed in claim 1, wherein cyclopentene or cyclohexene is used as hydrogen acceptor in the reaction of the compound IV to give the indene derivative I.

* * * * *